United States Patent

Dugstad et al.

Patent Number: 5,919,434
Date of Patent: Jul. 6, 1999

[54] POLYMERIC SURFACTANT-ENCAPSULATED MICROBUBBLES AND THEIR USE IN ULTRASOUND IMAGING

[75] Inventors: Harald Dugstad; Per Antonius Foss; Jo Klaveness, all of Oslo; Pål Rongved, Nesoddtangen; Roald Skurtveit, Oslo, all of Norway

[73] Assignee: Nycomed Imaging AS, Oslo, Norway

[21] Appl. No.: 08/602,797

[22] PCT Filed: Sep. 5, 1994

[86] PCT No.: PCT/GB94/01923

§ 371 Date: Mar. 14, 1997

§ 102(e) Date: Mar. 14, 1997

[87] PCT Pub. No.: WO95/06518

PCT Pub. Date: Mar. 9, 1995

[30] Foreign Application Priority Data

Sep. 3, 1993 [GB] United Kingdom .................. 9318288

[51] Int. Cl.⁶ ............................. A61K 49/04; A61K 9/16; B01J 13/02; B32B 5/16
[52] U.S. Cl. .......................... 424/9.52; 424/489; 424/501; 427/213.3; 427/213.36; 428/402.21
[58] Field of Search .................................. 424/9.52, 9.51, 424/9.5, 451, 489, 490, 497; 264/4, 4.1, 5; 600/458; 427/213.3, 213.36; 428/402.21

[56] References Cited

U.S. PATENT DOCUMENTS

| | | |
|---|---|---|
| 4,466,442 | 8/1984 | Hilmann . |
| 4,900,540 | 2/1990 | Ryan . |
| 5,088,499 | 2/1992 | Unger . |
| 5,271,928 | 12/1993 | Schneider . |
| 5,413,774 | 5/1995 | Schneider et al. ..................... 424/9.51 |
| 5,425,366 | 6/1995 | Reinhardt . |
| 5,543,158 | 8/1996 | Gref et al. ............... 424/501 |
| 5,558,854 | 9/1996 | Quay . |
| 5,639,443 | 6/1997 | Schutt et al. ........................ 424/9.52 |
| 5,730,954 | 3/1998 | Albayrak . |

FOREIGN PATENT DOCUMENTS

| | | |
|---|---|---|
| A-0 441468 | 8/1991 | European Pat. Off. . |
| A-0 458 745 | 11/1991 | European Pat. Off. . |
| A-0 535 534 | 4/1993 | European Pat. Off. . |
| WO-A-92 04392 | 3/1992 | WIPO . |
| WO-A-92 11873 | 7/1992 | WIPO . |
| WO-A-92 17212 | 10/1992 | WIPO . |
| WO-A-92 17213 | 10/1992 | WIPO . |
| WO-A-93 17718 | 9/1993 | WIPO . |
| WO-A-93 18070 | 9/1993 | WIPO . |
| WO-A-93 25242 | 12/1993 | WIPO . |

OTHER PUBLICATIONS

Langmuir, Hurter & Hatton, vol. 8, pp. 1291–1299 (1992) (copy appended).
Merck Index, p. 1090, Tenth Edition (1983).

*Primary Examiner*—José G. Dees
*Assistant Examiner*—Michael G. Hartley
*Attorney, Agent, or Firm*—Bacon & Thomas, PLLC

[57] ABSTRACT

The present invention relates to polymer-based gas-containing contrast agents in which microbubbles of gas are encapsulated by non-polymerizable wall-forming block or graft copolymer surfactants. The polymer surfactants are preferably biodegradable and include block and graft copolymers containing linkages of formula (I):

$$-(O)_m-CO-O-C(R^1R^2)-O-CO-(O)_n- \quad (I)$$

where $R^1$ and $R^2$ each represent a hydrogen atom or a carbon-attached monovalent organic group, or $R^1$ and $R^2$ together form a carbon-attached divalent organic group and m and n are each zero or 1.

3 Claims, No Drawings

POLYMERIC SURFACTANT-ENCAPSULATED MICROBUBBLES AND THEIR USE IN ULTRASOUND IMAGING

This invention relates to novel contrast agents, more particularly to gas-containing contrast agents of use in diagnostic imaging, and to novel polymers useful in their manufacture.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars, or by entraining or encapsulating the gas or a precursor therefor in a variety of polymer systems, e.g. as gas-containing polymer microparticles.

Thus, for example, WO 80/02365 discloses the use of gelatin encapsulated gas microbubbles for enhancing ultrasonic images. Such microbubbles do not, however, exhibit adequate stability at the dimensions preferred for use in echocardiography (1–10 μm) in view of the thinness of the encapsulating coating.

U.S. Pat. No. 4,774,958 discloses the use of microbubble dispersions stabilised by encapsulation in denatured protein, e.g. human serum albumin. Such systems permit the production of microbubble systems having a size of e.g. 2–5 μm but still do not permit efficient visualisation of the left heart and myocardium. The use of such protein-derived agents may also create problems with regard to potential allergenic reactions.

EP-A-0327490 discloses, inter alia, ultrasonic contrast agents comprising a microparticulate synthetic biodegradable polymer containing a gas or volatile fluid (i.e. having a boiling point below 60²⁰ C.) in free or bonded form. Representative synthetic biodegradable polymers include polyesters of hydroxy carbonic acids, polyalkyl cyanoacrylates, polyamino acids, polyamides, polyacrylated saccharides and polyorthoesters.

Similar biodegradable microparticulate polymers, based on polymerised aldehydes, are described in EP-A-0441468, while systems based on microparticulate poly(amino acid)—poly(cyclic imide) derivatives are described in EP-A-0458079.

Ultrasonic contrast agents consisting of microparticles consisting of amyloses or synthetic biodegradable polymers and a gas or volatile fluid are described in WO 89/06978.

EP-A-0458745 discloses air or gas-filled microballoons in which the encapsulating material is a deformable and resilient interfacially deposited polymer which is preferably biodegradable, examples including polysaccharides, polyamino acids, polylactides, polyglycolides, lactide/lactone copolymers, polypeptides, proteins, polyorthoesters, polydioxanone, poly-β-aminoketones, polyphosphazenes, polyanhydrides and poly(alkyl cyanoacrylates). The microballoons are normally prepared by emulsion techniques leading to deposition of the polymer around droplets of a volatile liquid which is subsequently evaporated. Such techniques generally involve the use of surfactants, for example lecithins, fatty acids or esters thereof with polyoxyalkylene compounds such as polyoxyethylene glycol or polyoxypropylene glycol, in order to stabilise the emulsion.

It is generally acknowledged that polymer-based contrast agents should desirably be biodegradable in order to facilitate their ultimate elimination from or absorption by the test subject. In many instances it has therefore been proposed to use polymers such as polyesters, polyanhydrides, polycarbonates, polyamides and polyurethanes which are biodegradable as a result of the susceptibility of ester, amide or urethane groups therein to enzymic hydrolysis in vivo.

In our published International Patent Application No. WO 93/17718 there are described polymer-based contrast agents which are designed to exhibit high and controllable levels of biodegradability in vivo by virtue of the presence in the polymer of methylene diester units of formula

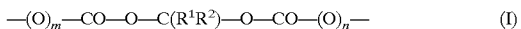

$$-(O)_m-CO-O-C(R^1R^2)-O-CO-(O)_n- \qquad (I)$$

(where $R^1$ and $R^2$ each represent a hydrogen atom or a carbon-attached monovalent organic group or $R^1$ and $R^2$ together form a carbon-attached divalent organic group and m and n are each zero or 1). Such units are particularly rapidly degraded by common esterase enzymes but are relatively stable in the absence of enzymes.

These polymers may be formulated into microparticle- and/or microballoon-containing contrast agents by, for example, emulsion techniques such as those described in the above-mentioned EP-A-0458745. It will normally be necessary for a dispersing agent, e.g. a surfactant, to be present during such processing; provided that the surfactant is physiologically acceptable it may, if desired, be retained in the final product, for example to enhance the dispersibility and/or stability of the contrast agent microparticles and/or microballoons in the intended carrier medium.

WO 92/17212 describes polymer-based contrast agents comprising microbubbles of gas or a gas precurser encapsulated by non-proteinaceous crosslinked or polymerised amphiphilic moieties, which may if desired contain methylene diester units of formula (I) as described above. These contrast agents may, for example, be prepared by emulsifying a polymerisable amphiphile, e.g. so as to yield an oil-in-water emulsion in which a volatile water-immiscible organic solvent is encapsulated by the amphiphilic moieties, e.g. in the form of micelles, and thereafter crosslinking or polymerising the amphiphilic moieties and, if desired, removing the volatile organic solvent, e.g. by evaporation. It will be appreciated that the surface active properties of the polymerisable amphiphiles may render unnecessary the use of extraneous surfactants in the emulsification procedures of such processes. The polymerisable amphiphiles may, for example, themselves contain polymer groupings, e.g. hydrophilic polymer groups such as polyoxyethylene chains, as well as polymerisable groupings, e.g. (meth)acrylic or other polymerisable alkenyl or alkynyl groups, and hydrophobic groups such as long chain alkyl groups.

The present invention is based on the finding that polymer-based gas-containing contrast agents in which microbubbles of gas are encapsulated by non-polymerisable wall-forming block or graft copolymer surfactants possess a number of advantageous properties. Thus such contrast agents may exhibit excellent storage stability and good stability and contrast effect in vivo following administration, often for several passages of circulation in the case of administration by intravenous injection; they can be designed to undergo rapid biodegradation thereafter. Moreover, it is possible by selection of the nature and size of the various regions or domains of the block or graft copolymer to influence properties of the contrast agents such as their stability, dispersibility, biological properties etc.

The fact that contrast agents according to the invention may readily and easily be prepared directly from block or graft copolymer surfactants, e.g. as described hereinafter, is also advantageous. Thus the use of prepolymerised wall-forming copolymer surfactant starting materials avoids the need for crosslinking or polymerisation reactions, e.g. as are described in WO 92/17212, with the attendant need subsequently to remove by-products and/or residues from materials such as initiators from the products in order to render them physiologically acceptable; contrast agents obtained directly from polymer starting materials may also exhibit greater structural integrity than contrast agents obtained by crosslinking or polymerisation reactions. Furthermore, as a result of the surface active properties of the block or graft copolymer surfactant starting materials, it is possible to prepare contrast agents according to the invention by emulsification techniques without using extraneous surfactants/emulsifiers, although as will be described hereinafter use of such emulsifiers is not precluded where desired in specific embodiments of the invention.

According to one aspect of the present invention there is provided a contrast agent comprising gas microbubbles encapsulated by a non-polymerisable wall-forming block or graft copolymer surfactant.

The term "non-polymerisable" as used herein in respect of the copolymer surfactant indicates that this material will not normally undergo further polymerisation e.g. during preparation or use of contrast agents according to the invention. It will be appreciated that the copolymer surfactant may, however, be capable of further polymerisation reactions under more extreme conditions than will be encountered in such circumstances.

The term "wall-forming" as used herein in respect of the copolymer surfactant indicates that this material is inherently capable of interacting to form an encapsulating structure having a desired degree of integrity without requiring chemical reactions such as crosslinking or further polymerisation to stabilise the structure. Such structures may, for example, take the form of solid microparticles, e.g. comprising one or more encapsulated gas microbubbles, or membranes or films encapsulating gas microbubbles dispersed in a liquid carrier.

The surfactant properties of copolymers used in contrast agents according to the invention will normally arise from the presence in the copolymer of separate regions or domains having different lyophilicity. Most commonly one or more such regions or domains will be hydrophilic and one or more other regions or domains will be hydrophobic, such that the copolymer exhibits amphiphilic properties. It may, however, also be possible to use copolymers containing separate regions or domains exhibiting, for example, differing degrees of hydrophilicity.

Block copolymer surfactants which may be used in contrast agents according to the invention include block copolymers having two or more blocks of differing lyophilicity, for example in linear di-block, tri-block or multi-block arrays, e.g. of the type A-B, A-B-A, B-A-B or A-B-A-B-A-B where A and B are polymer blocks of differing lyophilicity, e.g. hydrophilic and hydrophobic blocks respectively. Branched structures, e.g. of the type

and macrocyclic structures, e.g. of the type

may also be employed.

The size of one or other type of block may if desired be chosen to be relatively small in order to obtain a desired hydrophilic/lipophilic balance. Thus, for example, in the case of block copolymers containing hydrophilic and hydrophobic blocks it may be advantageous to select small-sized hydrophobic blocks in order to render the copolymer water-soluble.

In general where small-sized blocks are present these may include both oligomeric groups and quasi-polymeric groups, including monomeric groups, which may for example exhibit polymer characteristics (e.g. as a result of the presence of long chain units) while not strictly possessing a definable repeating unit. Copolymers containing such oligomeric or quasi-polymeric blocks are sometimes described in the art as "extended polymers". One category of such extended polymers useful in contrast agents according to the invention comprises hydrophilic polymer blocks linked by oligomeric or quasi-polymeric hydrophobic regions or domains.

Graft copolymer surfactants which may be used in contrast agents according to the invention will normally comprise a first polymer having branches of a second polymer of different lyophilicity along its length; if desired either the first or second polymer may be a block copolymer, in which case the surfactant may be termed a block-graft copolymer. One useful type of graft copolymer surfactant comprises a hydrophobic polymer backbone having branches of a hydrophilic polymer along its length.

Copolymer surfactants in contrast agents according to the invention may, for example, contain hydrophilic regions or domains derived from polymers such as polysaccharides, polyalcohols (e.g. polyvinyl alcohol), polyvinylpyrrolidone, polyethylene glycol and polyaminoacids. Polymers such as polyorthoesters, polyacetals, polyanhydrides, polyglycolic acids, poly(meth)acrylic acids and derivatives such as esters thereof, substituted as necessary by hydrophilic groups, may also be useful. Contrast agents comprising copolymer surfactants in which the hydrophilic regions or domains consist essentially of polyethylene glycol units may be particularly advantageous.

The presence of charged groups within the hydrophilic regions or domains may be advantageous since their high water-solubility may permit use of relatively small hydrophilic regions or domains; interactions between such charged species may also enhance the stability of dispersions of the copolymer surfactant by inhibiting aggregation.

Hydrophobic regions or domains in copolymer surfactants used in contrast agents according to the invention may, for example, be derived from oil-soluble condensation, ionic and free-radical generated polymers, for example poly (meth)acrylate esters, polyorthoesters, vinylic and styrenic polymers, polyacetals, polyanhydrides, polyglycolic acids and ethers and esters thereof, and polylactic acid/ polyglycolic acid copolymers; such polymers may, for example, incorporate or be substituted with hydrophobic groups such as alkyl, aralkyl or aryl groups to increase their hydrophobicity. The hydrophobic regions or domains may advantageously comprise a polyester chain (which may be an oligomeric or quasi-polymeric moiety) containing one or more long chain aliphatic groups (e.g. $C_{10-20}$ polymethylene groups).

The size of the hydrophobic blocks may particularly influence the wall-forming properties of copolymer surfactants which have low water-solubility, e.g. where these properties are (at least in part) the result of hydrophobic interactions. The physical state of the hydrophobic block, e.g. whether it tends to form crystal or amorphous structures and the degree of hardness or softness thereof, may also be of importance.

The different regions or domains of the copolymer surfactant may be joined directly or through a linker, e.g. comprising a polyvalent atom or inorganic group or a multifunctional organic group such as a monomer unit occurring in one of the regions or domains.

As has previously been noted, polymer-based contrast agents should desirably be biodegradable in order to facilitate their ultimate elimination from or absorption by the test subject. The contrast agents of the invention are therefore preferably biodegradable, i.e. comprise copolymer surfactants which incorporate groups or bonds which are labile in vivo. The copolymer surfactants may therefore, for example, advantageously contain acid-labile bonds, e.g. as in polyorthoesters, polyacetals, polyanhydries, polyglycolic acids and ethers, esters and polylactic acid copolymers thereof. Other potentially useful copolymer components exhibiting biodegradability include polysaccharides, polyaminoacids, polylactides, lactide/lactone copolymers, polypeptides, proteins, polydioxanones, poly-β-aminoketones, polyphosphazenes, and poly(alkyl cyanoacrylates).

A particularly useful class of copolymer surfactants in contrast agents according to the invention contain enzymically biodegradable methylene diester groups, e.g. of formula (I) as defined above. Examples of such grous are described in the aforementioned published International Patent Applications Nos. WO 92/04392 and WO 93/17718, the contents of which are incorporated herein by reference.

In such units of formula (I) $R^1$ and $R^2$ (when other than hydrogen) may, for example, each represent a carbon-attached hydrocarbyl or heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic group such as an aralkyl group (preferably having up to 20 carbon atoms), an aryl group (preferably having up to 20 carbon atoms) or a heterocyclic group having up to 20 carbon atoms and one or more heteroatoms selected from O, S and N. Such a hydrocarbyl or heterocyclic grouping may carry one or more functional groups such as halogen atoms or groups of the formulae —$NR^3R^4$, —$CONR^3R^4$, —$OR^5$, —$SR^5$ and —$COOR^6$, where $R^3$ and $R^4$ are each hydrogen atoms, acyl groups or hydrocarbyl groups as defined for $R^1$ and $R^2$; $R^5$ is a hydrogen atom, an acyl group or a group as defined for $R^1$ or $R^2$; and $R^6$ is a hydrogen atom or a group as defined for $R^1$ or $R^2$. Where $R^1$ and $R^2$ represent a divalent grouping this may, for example, be an alkylidene, alkenylidene, alkylene or alkenylene group (preferably having up to 10 carbon atoms), which may carry one or more functional groups as defined above.

One preferred class of units of formula (I) comprises those in which $R^1$ and $R^2$ are each selected from hydrogen atoms and methyl groups, e.g. in which $R^1$ represents a hydrogen atom and $R^2$ represents a methyl group.

If desired the properties of the wall-forming polymer may be modified by a softener or elasticiser as described in EP-A-0458745.

Any biocompatible gas may be employed in the contrast agents of the invention, for example air, nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. Use of perfluoroalkanes such as perfluorobutane or perfluoropentane may be advantageous. The gas may be free within the encapsulating structure formed by the copolymer surfactant or may be entrained in a containing structure within the encapsulating structure. It will be appreciated that the term "gas" as used herein includes any substance which is in gaseous form at the normal human body temperature of 37° C.

The contrast agents of the invention may if desired incorporate one or more additional emulsifiers, for example selected from fatty acids (e.g. straight chain saturated or unsaturated fatty acids, for example containing 10–20 carbon atoms) and carbohydrate and triglyceride esters thereof, phospholipids (e.g. lecithin), proteins (e.g. albumins such as human serum albumin), polyethylene glycols and block copolymers (e.g. poly(oxyethylene)-poly(oxypropylene)-poly(oxyethylene) block copolymers such as Pluronics), including extended polymers. Block copolymer emulsifiers may, for example, have a similar gross composition to a block copolymer used as the wall-forming polymer surfactant, but may exhibit a different hydropholic/lipophilic balance as a result of, for example, different ratios between the contents of hydrophilic and hydrophobic blocks.

Microparticulate contrast agents of the invention may if desired be coated, for example with one or more coating materials such as polyethylene glycols, proteins or polysaccharides, e.g. to modify their aggregation tendencies and/or biological properties.

Contrast agents according to the invention may be used in a variety of diagnostic imaging techniques, including ultrasound, MR and X-ray imaging. Their use in diagnostic ultrasonic imaging and in MR imaging, e.g. as susceptibility contrast agents, constitute preferred features of the invention.

For ultrasonic applications such as echocardiography, in order to permit free passage through the pulmonary system and to achieve resonance with the preferred imaging frequency of about 0.1–15 MHz, it may be convenient to employ microbubbles having an average size of 0.1–10 μm, e.g. 1–7 μm. Substantially larger bubbles, e.g. with average sizes of up to 500 μm, may however be useful in other applications, for example gastrointestinal imaging or investigations of the uterus or Fallopian tubes.

Microparticulate contrast agents according to the invention may, for example, be stored and transported in dry form, in which condition they will normally be stable indefinitely, being mixed with an appropriate liquid carrier (e.g. sterile water for injection, physiological saline or phosphate buffer) prior to administration. In this way the concentration of the injected or otherwise administered contrast agent may be varied at will, depending on the precise nature of the intended application. Contrast agents of the invention may also be stored in suspension in such carriers, especially when the porosity of the encapsulating polymer membrane is comparatively low, and/or the encapsulated gas has low solubility in the carrier liquid.

The contrast agents of the invention may be prepared by any convenient process. Such processes, which in general will involve interacting a gas with a non-polymerisable wall-forming block or graft surfactant so as to produce the desired contrast agent, constitute a further feature of the invention.

Representative microencapsulation techniques for the preparation of materials encapsulated by a wall or membrane of polymer material are described in literature such as "Microencapsulation and Related Drug Processes" by P. D. Deasy, Marcel Dekker Inc., New York (1984).

Contrast agents according to the invention may conveniently be prepared by emulsion techniques, e.g. such as are known in the polymer art. Such processes may typically involve (i) generating an emulsion comprising hydrophilic and hydrophobic phases wherein the copolymer surfactant is preferentially solubilised in the dispersed phase thereof or is distributed about the interfaces between said phases and (ii) obtaining the desired contrast agent from the emulsion. Single or multiple emulsions may be generated; in the latter case the copolymer surfactant will desirably be preferentially solubilised in or distributed about the interfaces of the finest (i.e. innermost) of the dispersed phases. Representative multiple emulsion techniques are described in WO 93/17718.

The hydrophilic/lipophilic balance of copolymer surfactant starting materials may be selected to give copolymers appropriate to a particular form of emulsion processing. Thus, for example, the processing of oil-soluble copolymer surfactants using oil-in-water emulsions may be advantageous. It may also be possible to use an oil-in-water emulsion to process a copolymer surfactant having a degree of water-solubility where the water-soluble blocks are such as to create strong attractive interactions which slow the kinetics of dissolution sufficiently to permit microparticle formation in the presence of water; a similar approach may be taken using a water-in-oil emulsion and a copolymer surfactant having a degree of oil-solubility.

Where it is desired to use copolymer surfactants which become distributed at the phase interfaces, e.g. in the form of a film or separate phase, it may be useful to employ copolymer surfactants capable of aggregation into liquid crystalline structures, e.g. as lamellar phases, hexagonal or reversed hexagonal phases, cubic phases, or other liquid or solid phases of copolymer surfactants in admixture with other components.

The hydrophobic phase of emulsions generated in accordance with this aspect of the process of the invention may, for example, comprise a water-immiscible organic solvent such as an aliphatic, cycloaliphatic or araliphatichydrocarbon, e.g. containing up to 10 carbon atoms, for example n-octane, cyclooctane, a dimethylcyclohexane, ethylcyclohexane, a methylheptane, an ethylhexane, toluene, xylene or a terpene, terpenoid or isoprenoid such as camphene or limonene; a haloalkane, such as methylene chloride, chloroform, carbon tetrachloride, methyl bromide or a Freon; an ester such as ethyl or propyl acetate, butyl formate or propyl or isopropyl butyrate or isobutyrate; or an appropriate ether or other lipophilic solvent.

The emulsion may, for example, be prepared using conventional techniques such as agitation, sonication, stirring (preferably high speed stirring) or other forms of mixing (e.g. high shear mixing), the copolymer surfactant advantageously being predissolved in what is to be the dispersed phase. It will be appreciated that factors such as stirring speed will influence the size of the encapsulated microbubbles ultimately produced; thus, for example, faster stirring tends to yield smaller microbubbles.

One useful embodiment of this process according to the invention comprises generating a single or multiple emulsion wherein the copolymer surfactant is preferentially distributed about the (where appropriate innermost) interfaces between the phases, and removing either the dispersed phase or both phases, e.g. by evaporation, spray drying or, more preferably, lyophilisation, to generate a desired microparticulate contrast agent. The emulsion, which may for example be an oil-in-water, water-in-oil or water-in-oil-in-water emulsion, may advantageously be lyophilised or otherwise treated under an atmosphere of the gas which is to be incorporated in the contrast agent, if desired at reduced pressure. Emulsifiers such as fatty acids and esters, phospholipids, proteins, polyethylene glycols and block copolymers (e.g. as hereinbefore described) may if desired be used in the emulsification process.

Where only the dispersed phase is removed in such a process the microparticles may be recovered from the dispersion phase by, for example, flotation or filtration.

In an alternative process a solution of the copolymer surfactant in an appropriate aprotic polar organic solvent (e.g. a sulphoxide such as dimethyl sulphoxide, a cyclic ether such as tetrahydrofuran or an N,N-disubstituted amide such as dimethylformamide) is mixed with an aqueous phase (e.g. using a high speed stirrer) so as to precipitate polymer material which may be collected and lyophilised to yield microparticulate contrast agents in accordance with the invention. The aqueous phase may advantageously contain a polymer material such as polyvinyl alcohol or poloxamer (e.g. a Pluronic). Such techniques are described in the above-mentioned EP-A-0458079.

A further process comprises injecting a solution of the copolymer surfactant in an appropriate organic solvent into liquid nitrogen; the solution may, if desired, also contain an additive such as hydroxypropylcellulose. Alternatively the copolymer surfactant may be dissolved in an appropriate solvent or dispersed in e.g. an oil-in-water, water-in-oil or multiple emulsion, and the solution or emulsion spray dried, e.g. as described in EP-A-0514790.

Coacervation techniques, e.g. as are known in the art, may also be employed in preparing contrast agents according to the invention.

Contrast agents of the invention may also be prepared by selecting copolymer surfactants having good film-forming properties as a result of their hydrophilic/lipophilic balances and molecular sizes and which therefore have the ability to self-organise into micellar or liposome-like structures. Such copolymer surfactants may be used to prepare solutions or dispersions of amphiphiles in laminar or lamellar form which may be used to generate gas-containing vesicles as described in WO 91/15244. Mixtures of copolymer surfactants with phospholipids (as well as synthetic biodegradable phospholipid derivatives of the copolymer surfactants, e.g. prepared as described by Laschewsky et al. in *J. Am. Chem. Soc.* 109 (1987), P. 788), optionally incorporating solubilising or viscosity-increasing agents such as glycerol, propylene glycol, glucose or lactose, may also be used for the preparation of echogenic vesicles, e.g. as described in EP-A-0554213.

In a still further variant of the process of the invention a gas-in-liquid emulsion is prepared in which the dispersed phase comprises the gas to be encapsulated and in which the copolymer surfactant is preferentially soluble in the liquid continuous phase, thereby generating a contrast agent comprising a dispersion of gas microbubbles stabilised by encapsulating copolymer surfactant. In a preferred embodiment of this process the gaseous dispersed phase is a hydrophobic perfluoroalkane such as perfluorobutane or perfluoropentane and the dispersion phase is an aqueous solution of a water-soluble copolymer surfactant, e.g. an extended polymer.

Copolymer surfactants useful in the preparation of contrast agents according to the invention may, for example, be prepared by methods known in the art, e.g. as described in Polymer Surfactants by Irja Piirma (Surfactant Science Series Vol. 42—Marcel Dekker, New York, 1992), the contents of which are incorporated herein by reference. Thus, for example, block copolymers may be prepared by techniques such as the active end group approach, anionic polymerisation, cationic polymerisation or condensation of prepolymers. Graft copolymers may, for example, be prepared by copolymerising a macromonomer comprising a polymer terminating at one end in a polymerisable group with a second monomer or by "grafting onto" or "grafting from" methods. Suitable block and block-graft copolymers are described in "Block Copolymers" by D. C. Allport & W. H. Janes, (Applied Sciences Publishers Ltd., London 1973).

The hydrophilic/lipophilic balance of the copolymer surfactants will be determined by factors such as the nature of the polymers constituting the different blocks and the relative ratio between the total volumes of e.g. hydrophilic and hydrophobic blocks. This balance may therefore be selected to give polymers appropriate to a particular form of emulsion processing, e.g. as described above.

Block and graft copolymer surfactants containing biodegradable linkages of formula (I) as hereinbefore defined are themselves novel and constitute a further feature of the present invention, as do emulsions comprising such copolymer surfactants, e.g. emulsions comprising phases of differing lyophilicity wherein the copolymer surfactant is preferentially solubilised in the dispersed phase thereof or is distributed about the interfaces between said phases. Most commonly the phases will be hydrophilic and hydrophobic respectively, although the copolymer surfactants may also be used to stabilise oil-in-oil emulsions of immiscible oils.

The novel copolymer surfactants according to the invention may, for example, contain representative or preferred atoms/groups $R^1$ and $R^2$ and hydrophilic and hydrophobic regions or domains as hereinbefore described. The biodegradable linkages may for example comprise units of formula

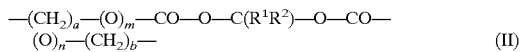

(II)

(where $R^1$, $R^2$, m and n are as hereinbefore defined and a and b are each integers in the range 1–30, preferably 10–18).

Preferred copolymer surfactants in accordance with this embodiment of the invention are block copolymers, including extended polymers. In addition to their usefulness as starting materials for the preparation of contrast agents according to the invention these novel block copolymer surfactants containing biodegradable linkages of formula (I) may have a wide range of further utilities, e.g. by analogy with known block copolymer surfactants (see for example Encyclopedia of Polymer Science Vol. 2 pp. 412–434—John Wiley and Sons, New York (1985)).

Block copolymer surfactants in accordance with the invention may therefore find use in applications such as foods, e.g. in water-in-oil emulsions such as mayonnaise and margarine and oil-in-water emulsions such as synthetic milk and ice cream; paints, coatings and impregnations, e.g. as dispersing agents for pigments or as biodegradable coatings to impart properties such as water-resistance or a glossy finish to materials such as paper or cardboard; cosmetics, e.g. moisturising cream and make-up; detergents, e.g. for general washing and cleaning as in laundry applications, or for dispersal of oil spills; phase transfer catalysts; drug formulations, e.g. as dispersants, solubilisers, gelling agents and emulsifying agents for drugs (including water-insoluble drugs); drug delivery systems, e.g. as carriers (including micellar carriers) to promote site-specific delivery and/or delayed release of drugs, where appropriate with concomitant reduction in toxic side effects; surgical materials such as implants, wound dressings, adhesives and the like, e.g. controlled release implants, implants for fracture fixation, tendon and ligament replacements, biodegradable dressings, dressings with controlled release, sutures, controlled release creams and ointments, adhesives and bone cements; particle coatings, e.g. to provide targetting of an active therapeutic agent to a desired site such as the lymphatic system; coating of medical devices, e.g. to promote protein resistance; textiles, e.g. as antistatic agents; thermoplastic elastomers (in contrast to conventional non-melt processable crosslinked elastomers) which may be used to manufacture slowly biodegradable replacement body parts such as blood vessels by thermal processing; biodegradable clear packaging films, wherein the domain sizes for the polymer blocks are less than the wavelength of visible light; polymer property modifiers, e.g. as dispersed particles in another polymer matrix, for example to modify the fracture properties thereof; self-lubricating materials, e.g. wherein biodegradation generates low molecular weight compounds which provide a lubricating effect; compatibilisers for polymer blends, e.g. to facilitate dispersion of one polymer in another (the biodegradability of the copolymer surfactant may be utilised to accelerate degradation of an otherwise relatively stable polymer blend); separation membranes exhibiting selective transport properties, e.g. as wound coatings permitting transport of gas to the wound but providing a barrier to dirt and infection; anti-fouling coatings, e.g. such that continuous controlled biodegradation from the surface prevents adhesion of organisms, secondary toxic components optionally being incorporated to provide further protection through controlled release thereof; foam-forming materials, e.g. for dispersing blowing agents or producing biodegradable foams useful for introducing cells in, for example, bone marrow, pancreas, liver and cartilage transplants; antifoams, e.g. for use in machine dishwashing and the sugar beet industry; and in the manufacture of hydrogels, e.g. for use in the controlled release of drugs or agrochemicals, in cosmetics and toiletries, and as highly absorbent materials, e.g. for nappies or spill containment.

The following non-limitative Examples serve to illustrate the invention.

List of Abbreviations

AIBN: 2,2'-azobisisobutyronitrile

DMF: N,N-dimethylformamide

DBU: 1,8-diazabicyclo[5.4.0]undec-7-ene(1,5-5)

GPC: gas phase chromatography $MgSO_4$: magnesium sulphate

Mp: melting point
PEG: polyethylene glycol
THF: tetrahydrofuran
SEC: size exclusion chromatography
Mw: weight average molecular weight
Mn: number average molecular weight

EXAMPLE 1

Preparation of Intermediates and Pre-polymers a) Methylene bis(16-hydroxyhexadecanoate)

To a solution of 16-hydroxyhexadecanoic acid (15.0 g, 0.055 mol) in DMF (200 ml), DBU (8.65 g, 0.055 mol) was added at room temperature. After 5 minutes with stirring, diiodomethane (7.37 g, 0.028 mol) was added. The mixture was left with stirring at room temperature for 2 days. DMF was evaporated under reduced pressure and the residue dissolved by adding chloroform (100 ml) and water (50 ml). After separating the phases the aqueous layer was extracted with chloroform (3×100 ml) and the combined organic phases were dried ($MgSO_4$). The solvent was removed under reduced pressure and the residue recrystallised from ethyl acetate to give 10.17 g (65%) of the title product as a white solid. Mp: 96.2° C. $^1$HNMR (300 MHz, $CDCl_3$): δ 1.2–1.4 (m, 44H), 1.5–1.6 (m, 8H), 2.35 (t, 4H), 3.64 (t, 4H), 5.75 (s, 2H). $^{13}$CNMR (75 MHz, $CDCl_3$): δ 24.43, 25.55, 28.81, 29.42, 32.63, 33.80, 62.91, 78, 172.20.

b) Acid Chloride Terminated poly(methyl methacrylate) 1000

Acid terminated poly(methyl methacrylate) was synthesised by a matched chain transfer polymerisation. 2-Ethoxyethanol (160 g) was heated to 120° C. To this a mixture of 2-ethoxyethanol (80 g), methyl methacrylate (160 g, 1.6 mol), thioglycollic acid (14.4 g, 0.156 mol) and 4,4'-azobis(4-cyanopentanoic acid) (14.4 g, 0.1 mol) was added over a period of 1.5 hours. The reaction was held at 120° C. for a further 0.5 hours before cooling to room temperature. The polymer was precipitated into a cold solution of sodium chloride (5% w/v). The polymer was purified by repeated precipitation from hot methanol into cold distilled water (3 times). End group analysis gave a number average molecular weight of 910 Daltons.

Acid terminated poly(methyl methacrylate) (105 g, 0.115 mol) was dissolved in dry toluene (300 ml). The solution was cooled to 0° C. and oxalyl chloride (15 g, 0.118 mol) was added slowly. The reaction was permitted to warm to room temperature, whereafter the excess oxalyl chloride was removed under reduced pressure to yield the title product.

c) α-Methacryloyl-ω-methoxy (PEG) 2000

Dry α-Hydroxy-ω-methoxy PEG 2000 (6.40 g, 3.20 mmol) was dissolved in THF (160 ml) and the solution cooled to 10̃20 C. Pyridine (0.38 g, 4.78 mmol) was diluted with THF (4 ml) and added to the solution under a dry nitrogen atmosphere. Methacryloyl chloride (0.50 g, 4.78 mmol) was diluted in THF (12 ml) and added dropwise. The temperature was gradually raised to room temperature and the mixture was left with stirring for 24 hours. The reaction mixture was filtered and the remaining acid chloride and solvent removed under reduced pressure. The residue was dissolved in THF and precipitated by addition of ether to give 4.50 g (68%) of the title product.

d) Bimetallic μ-Oxoalkoxide Catalyst: $Zn\{OAl[OCH(CH_3)_2]_2\}_2$

Following the method of U.S. Pat. No. 3,432,445, anhydrous zinc acetate (23.00 g, 125.4 mmol) was added to a solution of aluminium isopropoxide (51.20 g, 250.7 mmol) in decahydronaphthalene (130 ml). The mixture was heated to 190° C. with stirring under nitrogen and the reaction allowed to proceed for three hours during which about 20 ml distillate was collected in the boiling range 73–88° C. The decahydronaphthalene was then removed under reduced pressure at 160–180° C. The product, a resinous orange solid, was dissolved in distilled n-heptane and the solution centrifuged to remove any remaining solids. A typical preparation gave low yield (23%) and analysis for Al and Zn content gave a mole ratio of Al/Zn of 1.98.

e) Ethylidene bis[16-(5-chlorocarbonylpentanoyloxy)-hexadecanoate]

In a three-necked round bottomed flask equipped with a reflux condenser, a glass gas inlet tube and a pressure equalizing dropping funnel was placed freshly distilled adipoyl chloride (2.60 ml, 17.50 mmol) dissolved in absolute chloroform (15 ml). The temperature was raised to ca. 50° C. and under a gentle stream of nitrogen through the solution, a solution of ethylidene bis(16-hydroxyhexadecanoate) (1.0 g, 1.75 mmol) in absolute chloroform (30 ml) was added dropwise and left at this temperature a further 3 hours after addition. The mixture was then cooled to room temperature and quickly transferred into a 50 ml round bottomed flask equipped for distillation under reduced pressure. Chloroform was first distilled off at normal pressure, then oil-pump vacuum was established and excess adipoyl chloride distilled off at ca. 75° C., 5 mbar pressure, leaving the residual title compound (1.56 g).

f) 16-Hexadecanoyloxyhexadecanoic Acid

16-Hydroxyhexadecanoic acid (5.43 g, 19.9 mmol) was dissolved in tetrahydrofuran (190 ml) and pyridine (2.36 g, 29.9 mmol) was added. Palmitoyl chloride (5.48 g, 19.9 mmol) was dissolved in tetrahydrofuran (10 ml) and added dropwise at room temperature. After stirring at room temperature for 16 hours, the mixture was filtered and the filtrate evaporated under reduced pressure. The residue was dissolved in chloroform, washed with water (3×50 ml), and the organc phase was dried ($MgSO_4$). After evaporating under reduced pressure, the residue was purified on a silica column, eluted with chloroform with increasing methanol concentration (from 1% to 2% methanol in chloroform) to give 8.41 g (83%) of the title compound. $^1$H NMR (300 MHz, $CDCl_3$): δ 0.85 (t, 3H, $CH_3$), 1.20–1.35 (s, 46H, —$CH_2$—), 1.55–1.70 (m, 6H, —$CH_2$—), 2.25 (t, 2H, —$CH_2$—C(O)—O), 2.45 (t, 2H, —C$\underline{H}_2$—COOH), 4.05 (t, 2H, —O—$CH_2$). $^{13}$C NMR (75 MHz, $CDCl_3$): δ 14.01, 22.57, 24.10, 24.91, 25.82, 28.53, 28.75, 28.94, 29.08, 29.15, 29.25, 29.36, 29.54, 31.81, 34.29, 35.16, 64.27, 76.48, 76.90, 77.10, 77.32, 169.50, 173.91.

g) 16-Hexadecanoyloxyhexadecanoyl Chloride

16-Hexadecanoyloxyhexadecanoic acid (7.73 g, 15.13 mmol) prepared as in (f) above was dissolved in tetrahydrofuran (140 ml) and oxalyl chloride (4.80 g, 37.83 mmol) was added dropwise. The mixture was stirred at room temperature for 3 days and then the solvent and unreacted oxalyl chloride were evaporated under reduced pressure to give 8.0 g (100%) of the title compound.

h) 1-[16-(16-Hexadecanoyloxyhexadecanoyloxy)-hexadecanoyloxy]ethyl 16-hydroxyhexadecanoate Ethylidene bis (16-hydroxyhexadecanoate) (4.38 g, 7.67 mmol) was dissolved in THF (80 ml) and pyridine (0.61 g, 7.71 mmol) was added. 16-hexadecanoyloxyhexadecanoyl chloride (4.18 g, 7.90 mmol) was dissolved in THF (20 ml) and added dropwise. After 3 days at room temperature the mixture was filtered and the filtrate was left −20° C. for 2 hours. The precipitated product was filtered and purified by flash chromatography (silicagel, chloroform) to give 2.4 g (29%) of the title compound. $^1$H NMR (300 MHz, $CDCl_3$): δ 0.85 (t, 3H, $CH_3$), 1.2–1.4 (s, 90H, —$CH_2$—), 1.45 (d, 3H, —O—CH(C$\underline{H}_3$)—O—), 1.5–1.7 (m, 14H, —$CH_2$—), 2.25

(m, 8H, —CH$_2$—C(O)—O—), 3.60 (t, 2H, —C$\underline{H}_2$—OH), 4.05 (t, 4H, —C(O)—O—CH$_2$—), 6.85 (q, 1H, —O—C $\underline{H}$(CH$_3$)—O—). $^{13}$C NMR (75 MHz, CDCl$_3$): δ 13.7, 19.1, 22.2, 24.2, 24.6, 25.2, 25.5, 28.2, 28.5, 28.7, 28.8, 29.0, 29.2, 31.5, 32.3, 33.7, 34.0, 62.5, 64.0, 88.0, 171.5, 173.5.

i) Preparation of Methoxy-endcapped PEGs

Preparation of a Tyical Polymer (MeO-PEG 2000)

An initiator solution was prepared by careful addition of potassium metal (0.400 g, 10.23 mmol) to methanol (1.300 g, 40.57 mmol) in an inert atmosphere. This initiator solution (0.220 g, 1.32 mmol potassium methoxide) was injected into an ampoule containing ethylene oxide (10.000 g, 227.00 mmol). The sealed ampoule was allowed to stand at room temperature overnight. The temperature was then raised to 60° C. and reaction allowed for 72 hours. After removal of unreacted monomer, the contents of the ampoule were dissolved in dichloromethane and the solution neutralised with dilute aqueous hydrochloric acid. The polymer solution was washed three times with distilled water, rotary evaporated and then vacuum dried. Assignments for MeO-PEG polymers. $^1$H-NMR: δ 2.7 (OH), 3.2 (OCH$_3$), 3.5 (—CH$_2$— main chain), 3.4 (—C$\underline{H}_2$OCH$_3$). $^{13}$NMR: δ 58.5 (—OCH$_3$), 61.2 (—CH$_2$OH), 70.5 (—CH$_2$— main chain), 71.3 (—C$\underline{H}_2$OCH$_3$), 72.2 (—C$\underline{H}_2$CH$_2$OH). The GPC was recorded in THF and the molecular weight calibration was via PEG standards. GPC data for a typical sample: Mp: 2679, Mn: 2012, Mw: 2283. Polydispersity: 1.135.

j) General Procedure for Methoxy PEG Chloroformate

PEG 2000 monomethyl ether (6.00 g, 3.00 mmol) was dissolved in toluene (50 ml) and dried by refluxing in a Dean Stark apparatus. Pyridine (0.24 g, 3.00 mmol) was added at room temperature. Trichloromethyl chloroformate ("diphosgene") (0.60 g, 3.00 mmol) was dissolved in toluene (10 ml) and added dropwise. The mixture was stirred at room temperature for 12 hours and filtered. The solvent was evaporated under reduced pressure to give the title compound in quantitative yield.

EXAMPLE 2

Preparation of Block and Graft Copolymers a) PEG 5000-block-Polyester of Methylene bis(16-hydroxyhexadecanoate & adipoyl chloride-block-PEG 5000

Methylene bis(16-hydroxyhexadecanoate) (0.56 g, 1.0 mmol) and dry α-methoxy-ω-hydroxy PEG of number average molecular weight 5000 (0.5 g, 0.1 mmol) were dissolved in a mixture of xylene/trichloroethylene (80:20 100 ml), and heated to 60° C. Adipoyl chloride (0.192 g, 1.05 mmol) was added. The mixture was refluxed at reduced pressure and 60° C. for 24 hours. The polymer was recovered by fractional precipitation from xylene/trichloroethylene (80:20) at 4° C. The product was shown by SEC to have a Mn of 3800 and a Mw of 8000 (polystyrene equivalents).

b) PEG 2000-block-Polyester of Methylene bis(16-hydroxyhexadecanoate) & adipoyl chloride-block-PEG 2000 (Method 1)

Methylene bis(16-hydroxyhexadecanoate) (0.56 g, 1.0 mmol) and dry α-methoxy-ω-hydroxy PEG of number average molecular weight 2000 (0.0572 g, 0.0286 mmol) were dissolved in a mixture of xylene/trichloro-ethylene (80:20—100 ml), and heated to 60$_2$0 C. Adipoyl chloride (0.186, 1.014 mmol) was added. The mixture was refluxed at reduced pressure and 60$_2$0 C. for 24 hours. The polymer was recovered by fractional precipitation from xylene/trichloroethylene (80:20) at 4$_2$0 C. The product was shown by SEC to have a Mn of 3400 and a Mw of 12700 (polystyrene equivalents).

c) PEG 2000-block-Polyester of Methylene bis(16-hydroxyhexadecanoate & adipoyl chloride-block-PEG 2000 (Method 2)

Methylene bis(16-hydroxyhexadecanoate) (0.56 g, 1.0 mmol) was dissolved in a mixture of xylene/ trichloroethylene (80:20—100 ml), and heated to 60$_2$0 C. Adipoyl chloride (0.201, 1.1 mmol) was added. The mixture was refluxed at reduced pressure and 60° C. for 35 minutes. Dry α-methoxy-ω-hydroxy PEG of number average molecular weight 2000 (0.4 g, 0.2 mmol) was added to the reaction mixture. The mixture was refluxed at reduced pressure and 60° C. for a further 24 hours. The polymer was recovered by fractional precipitation from xylene/ trichloroethylene (80:20) at 4$_2$0 C. The product was shown by SEC to have a Mn of 5200 and a Mw of 17500 (polystyrene equivalents).

d) Di-block Copolymer of Poly(methyl methacrylate) 1000 and PEG 2000

α-Hydroxy-ω-methoxy PEG of number average molecular weight 2000 (40 g, 0.02 mol) was dissolved in toluene and dried with molecular sieve (4 Å). To this a solution of acid chloride terminated poly(methyl methacrylate) as produced in Example 1(b) (20 g, 0.02 mol) in toluene was added. The mixture was refluxed for 24 hours. The polymer was isolated by precipitation with petroleum ether (40–60). The polymer was purified by ion exchange (IRA-400, Fisons) and by dissolution in water, heating above the cloud point of the copolymer and decantation (three times). The product so obtained was finally dissolved in toluene and precipitated with petroleum ether (40–60) to yield the title product as a white powder.

e) Di-block Copolymer of Poly(methyl methacrylate) 1000 and PEG 4000

(α-Hydroxy-ω-methoxy PEG of number average molecular weight 4000 (80 g, 0.02 mol) was dissolved in toluene and dried with molecular sieve (4 Å). To this a solution of acid chloride terminated poly(methyl methacrylate) as produced in Example 1(b) (20 g, 0.02 mol) in toluene was added. The mixture was refluxed for 24 hours. The polymer was isolated by precipitation with petroleum ether (40–60). The polymer was purified by ion exchange (IRA-400, Fisons) and by dissolution in water, heating above the cloud point of the copolymer and decantation (three times). The product so obtained was finally dissolved in toluene and precipitated with petroleum ether (40–60) to yield the title product as a white powder.

f) Poly(Methyl methacrylate)-graft-PEG 2000

α-Methyacryloyl-ω-methoxy PEG of number average molecular weight 2000 as synthesised in Example 1(c) (0.50 g, 0.25 mmol) and AIBN (2 mg, 0.012 mmol) were dissolved in THF (3.0 ml) and degassed by repeated freezing, evacuation and thawing cycles (4 times). Methyl methacrylate (0.5 ml, 4.7 mmol) was distilled directly into the ampoule and the ampoule sealed. Polymerisation was performed in an oil bath at 60° C. for 22.75 hours.

The polymer was recovered by precipitation with petroleum ether (40–60) then purified by dissolving in a small amount of THF and adding to water (200 ml). On heating above 60° C. the polymer came out of solution. The title product was dried under reduced pressure.

g) Multi-block Copolymer of PEG and Poly(methylene-bis (16-hydroxyhexadecanoate) Plus Adipoyl Chloride (1:3:4)

1) Polyester formation

Methylene bis(16-hydroxyhexadecanoate) (1.392 g, 2.50 mmol) was dissolved in a xylene/trichloroethylene mixture (80:20), and heated to 60° C. Adipoyl chloride (0.610 g, 3.33 mmol) was added. The mixture was refluxed at reduced pressure and 60° C. for 4 hours.

2) Coupling of blocks to give multi block copolymer Dry α,ω di-hydroxy PEG 1500 (1.25 g, 0.833 mmol) was added to the reaction mixture from above. Refluxing at reduced pressure was continued for 2 days. The polymer was recovered by drying at reduced pressure. The residue was dissolved in dichloromethane and precipitated from methanol. SEC showed the product to have a Mn of 5600 and a Mw of 9400 (polystyrene equivalents) and that there was no evidence of the presence of PEG homopolymer. $^1$HNMR indicated formation of a block copolymer with a molar composition of 2.6:1 polyester to poly(ethylene oxide).

h) Di-block Copolymer of PEG 2000 and Poly(lactic acid) 2000

α-Hydroxy-ω-methoxy PEG 2000 (10.0 g, 5.0 mmol) was dissolved in toluene (300 ml) and dried by refluxing in a Dean and Stark trap for 12 hours. Poly(lactic acid) (Resomer L-104, Molecular weight 2000) (1.0 g, 0.5 mmol) and p-toluenesulfonic acid mono hydrate (2 mg, 0.001 mmol) were added. After Dean and Stark refluxing of the mixture for three days, the solvent was removed under reduced pressure, and the residue was washed with water and filtered.

i) Block Copolymer of Methylene bis(16-hydroxyhexadecanoate), Adipoyl Chloride and α-hydroxy-ω-methoxy PEG 2000

Methylene bis(16-hydroxyhexadecanoate) (8.0 g, 14.37 mmol) was dissolved in xylene/trichlorethylene (4:1) (250 ml) and heated to 6020 C. Adipoyl chloride (freshly distilled) (2.92 g, 15.97 mmol) was added dropwise and the mixture refluxed at 60° C. under vacuum (100 mbar) for 5 hours. Dry α-hydroxy-ω-methoxy PEG 2000 (6.39 g, 3.19 mmol) dissolved in toluene (58 ml) was added together with trichloroethylene (14 ml). The mixture was refluxed under vacuum (100 mbar) for another 14 hours. After cooling to room temperature and precipitating in a refrigerator, the mixture was filtered. The precipitate was dissolved in chloroform and precipitated once from hexane and then twice from methanol. A portion of the crude product (4.25 g) was dissolved in chloroform and precipitated once more from methanol to give the title compound (3.78 g): $^1$H NMR 200 MHz δ: 1.3 (s, CH$_2$), 1.5–1.7 (m, CH$_2$), 2.2–2.4 (m, CH$_2$CO), 3.6 (s, OCH$_2$CH$_2$O), 4.0–4.1 (m, CH$_2$O), 5.7 (s, OCH$_2$O). SEC: Mp=21,191; Mn=5,571; Mw=21,079 (polystyrene equivalents).

j) Block copolymer of methylene bis(16-hydroxyhexadecanoate), adipoyl chloride and α-hydroxy-ω-methoxy PEG 2000

Methylene bis(16-hydroxyhexadecanoate) (7.50 g, 13.47 mmol) was dissolved in xylene/trichlorethylene (4:1) (235 ml) and heated to 70° C. Adipoyl chloride (freshly distilled) (2.74 g, 14.97 mmol) was added dropwise and the mixture refluxed at 70° C. under vacuum (100 mbar) for 5 hours. Dry α-hydroxy-ω-methoxy PEG 2000 (5.99 g, 2.99 mmol) dissolved in toluene (53 ml) was added together with trichloroethylene (13 ml). The mixture was refluxed under vacuum (100 mbar) for another 40 hours. After cooling to room temperature and precipitating in a refrigerator, the mixture was filtered. The precipitate was dissolved in chloroform and precipitated once from hexane and then once from methanol. Half the crude product was purified by flash chromatography (silica, eluant: chloroform with stepwise increasing methanol concentration from 0 to 5%) giving the title compound (1.50 g). $^1$H NMR 300 MHz δ: 1.23 (s (br), CH$_2$), 1.57–1.65 (m, CH$_2$), 2.31–2.36 (m, CH$_2$CO), 3.37 (s, CH$_3$O), 3.63 (s, OCH$_2$CH$_2$O), 4.01–4.06 (m, CH$_2$O), 5.73 (s, OCH$_2$O). SEC: Mp=13,313; Mn=6,357; Mw=12,351, (polystyrene equivalents).

k) Block copolymer of ethylidene bis(16-hydroxyhexadecanoate), adipoyl chloride and α-hydroxy-ω-methoxy PEG 2000

Ethylidene bis(16-hydroxyhexadecanoate) (2.00 g, 3.50 mmol) was dissolved in xylene/trichlorethylene (4:1) (70 ml) and heated to 70° C. Adipoyl chloride (freshly distilled) (0.73 g, 3.99 mmol) was added dropwise and the mixture refluxed at 70° C. under vacuum (100 mbar) for 6 hours. Dry α-hydroxy-ω-methoxy PEG 2000 (1.72 g, 0.86 mmol) dissolved in toluene (15 ml) was added together with trichloroethylene (3 ml). The mixture was refluxed under vacuum (100 mbar) for another 40 hours. After cooling to room temperature and precipitating in a refrigerator, the mixture was filtered. The precipitate was dissolved in chloroform and purified by flash chromatography (silica, eluant: chloroform with 0.75% methanol) to give the title compound (0.42 g). $^1$H NMR 300 MHz δ: 1.24 (s (br), CH$_2$), 1.44 (d, CH$_3$—CH), 1.59–1.64 (m, CH$_2$), 2.26–2.31 (m, CH$_2$CO), 3.37 (s, CH$_3$O), 3.64 (s, OCH$_2$CH$_2$O), 4.04 (t, CH$_2$O), 6.85 (q, CH). SEC: Mp=12,410; Mn=3,830; Mw=8,715 (polystyrene equivalents).

l–r) Preparation of Di-block Copolymers: General Procedure

The di-block copolymers were prepared by sequential polymerization of ethylene oxide (EO) with caprolactone (CPL), of ethylene oxide with lactide (LD), and of ethylene oxide with caprolactone and lactide. The polymerisations were catalyzed by the bimetallic μ-oxoalkoxide as prepared in Example 1(d).

The dry solvent, toluene or tetrahydrofuran, was distilled into a flamed glass ampoule. Ethylene oxide was dried over calcium hydride and condensed into the glass ampoule under high vacuum. An appropriate quantity of catalyst, to give an ethylene oxide block of the desired length, was added by injection into the ampoule under a nitrogen atmosphere. The ampoule was sealed, heated to 6020 C. and the reaction allowed to proceed for 24 hours. Caprolactone, lactide, or caprolactone and lactide mixtures in tetrahydrofuran were next added by injection of an appropriate quantity into the ampoule under a nitrogen atmosphere. The ampoule was heated to 6020 C. for 24 hours, and then the polymerization was terminated by addition of isopropyl amine. The polymer solution was diluted with tetrahydrofuran and washed with dilute aqueous citric acid to remove catalyst residues. The polymer solution was further washed with distilled water until neutral and the high molecular weight polymer precipitated with n-heptane. The precipitated polymer was finally vacuum dried to yield a white polymer. The nature of the polymerizations performed and results are summarized in Table 1.

TABLE 1

| Ex. | Monomers parts by weight | | | | Cat/Mon | Conv | |
|---|---|---|---|---|---|---|---|
| | EO | CPL | LD | Diluent | mol % | % | MW by $^1$H-NMR |
| l | 1.0 | 7.6 | | toluene | 0.26 | 88 | EO1,000/CPL5,700 |
| m | 1.0 | 1.1 | | toluene | 0.30 | 93 | EO2,500/CPL2,800 |
| n | 1.0 | 3.0 | | THF | 0.32 | 74 | EO4,000/CPL12,000 |
| o | 1.0 | 1.7 | | toluene | 0.33 | 68 | EO3,000/CPL5,900 |
| p | 2.0 | 7.4 | 1.0 | THF | 0.44 | 48 | EO2,400/(CPL8,600-LD700) |
| q | 1.7 | | 1.0 | THF | 1.69 | 49 | EO6,400/LD900 |
| r | 1.4 | 1.0 | | THF | 1.82 | 56 | EO3,500/CPL500 | s) Polymerization catalyzed by aluminium isopropoxide

Aluminium isopropoxide (1.19 g, 5.8 mmol) was dried under high vacuum in a glass ampoule for 4 hours at room temperature. Dry toluene was distilled into the ampoule under high vacuum and dissolution of the aluminium isopropoxide allowed. Ethylene oxide (7.42 g, 168.6 mmol)

was dried over calcium hydride and condensed into the glass ampoule under high vacuum. The ampoule was sealed, heated to 45° C. and reaction allowed to proceed for 39 hours. Caprolactone (8.63 g, 75.6 mmol) was next added by injection into the ampoule under a nitrogen atmosphere. The ampoule was heated to 45° C. for a further 24 hours. The highly viscous product was dissolved in dichloromethane, the polymerization terminated with dilute aqueous acetic acid and the high molecular weight polymer precipitated with n-heptane. Molecular weight was determined by $^1$H-NMR indicating ethylene oxide and caprolactone block lengths at 500 and 5,200, respectively.

t–y) Preparation of Poly(Methyl Methacrylate)—graft-PEGs: General Procedure

α-Methacryloyl-ω-methoxy PEG 2,000 as synthesised in Example 1(c) was added to AIBN in a glass reactor and then evacuated. Toluene (ca. 40 ml) was distilled under vacuum into the reactor followed by destabilised methyl methacrylate (MMA) monomer. The reactor was sealed and then heated to 50° C. for approximately 20 hours. The title polymer was recovered by precipitation into heptane. It was purified by dissolving in a minimum amount of THF, adding this solution to water and then heating above the cloud point of the polymer, at which point the polymer came out of solution. This was repeated once. The prepared graft copolymers were characterised by $^1$H-NMR (Table 2):

TABLE 2

| Ex | Methacryoyl-PEG (g) | MMA monomer (ml) | AIBN (mg) | NMR Analysis PEG content (wt-%) |
|---|---|---|---|---|
| t | 4.0 | 4.0 | 6.6 | 34 |
| u | 2.0 | 4.0 | 6.6 | 24 |
| v | 4.0 | 2.0 | 3.5 | 50 |
| w | 3.0 | 4.5 | 8.1 | 27 |
| x | 4.5 | 3.0 | 5.7 | 41 |
| y | 0.5 | 10 | 16.5 | 1.3 | z) Random chain-extended polymer of PEG 1500, adipoyl chloride and ethylidene bis(16-hydroxyhexadecanoate) (0.37:1.85:1.75), multiblock To a suspension of ethylidene bis(16-hydroxyhexadecanoate) (1.0 g, 1.75 mmol) in dimethoxyethane (10 ml) at room temperature was added freshly distilled adipoyl chloride (270 μl, 1.85 mmol). The temperature of the mixture was gradually raised to 60° C., and a colourless solution obtained. After 5 hours at this temperature PEG 1500 (0.55 g, 0.37 mmol) was added and heating continued for a further 17 hours before the mixture was cooled to room temperature, the solvent evaporated and the solid residue stirred in petroleum ether (bp 40–60° C.) for 15 minutes and filtered to give the title compound (1.30 g) as a white solid.

aa) Extended polymer from PEG 1500 and ethylidene bis[16-(5-chlorocarbonylpentanoyloxy)hexadecanoate] (A-B-A)

Ethylidene bis[16-(5-chlorocarbonylpentanoyloxy) hexadecanoate] prepared as in Example 1(e) (0.88 g, 1.02 mmol) was dissolved in toluene (15 ml) in a 100 ml 3-necked round bottomed flask equipped with a glass gas inlet tube and a reflux condenser. PEG 1500 (3.06 g, 2.04 mmol) was added and the mixture heated at 60° C. for 22 hours, cooled to room temperature and the solvent removed under reduced pressure to give the title compound (4.12 g) as a white wax.

ab) Extended polymer from PEG 1500 and ethylidene bis[16-(5-chlorocarbonylpentanoyloxy)hexadecanoate] (multiblock)

The reaction was performed as in Example 2(aa), but with ethylidene bis[16-(5-chlorocarbonylpentanoyloxy) hexadecanoate (1.02 g, 1.18 mmol) in toluene (20 ml) and PEG 1500 (1.77 g, 1.18 mmol) to give the title compound (2.29 g) as a white wax.

ac–af) Extended polymer of PEG, adipic acid and ethylidene bis(16-hydroxyhexadecanoate) (random multiblock)

A solution of PEG 2000 (A) (4.14 g, 2.07 mmol) in 1,1,2-trichloroethylene (26 ml) was added via a syringe to a round bottomed flask containing ethylidene bis(16-hydroxyhexadecanoate) (B) (118 mg, 0.207 mmol), under nitrogen atmosphere. The resulting mixture was heated to 60° C., and when a clear solution had been obtained, adipoyl chloride (C) (417 mg, 2.277 mmol) was added via a syringe. The pressure was reduced to 250 mbar and the solution was stirred at 6020 C. over a period of 92 hours. Remaining hydrogen chloride, evolved in the reaction, and the solvent were removed on a rotatory evaporator at reduced pressure and 60° C. for 3 hours, and subsequently under vacuum (<0.1 mm Hg) at 60° C. for 24 hours. Finally, the polymer was precipitated from an acetone solution by adding petroleum ether, and cooling in an ice bath for 2 hours. Filtration yielded 3.5 g of the polymer as a white waxy solid.

In total four different block copolymers differing in the molecular weight of the starting PEGs were prepared by this method; the conditions specific for each polymerisation are given in Table 3 below. $^{13}$C NMR- and $^1$H NMR-spectra of the polymers was in agreement with the expected products.

TABLE 3

| Entry | Mw for starting PEG | Molar ratio A:B:C[1] | Solvent | Reaction time (hours) |
|---|---|---|---|---|
| ac | 400 | 10:1:11 | Diglyme-xylene | 21 |
| ad | 600 | 10:1:11 | Diglyme | 24 |
| ae | 1500 | 10:1:11 | DME | 21 |
| af | 2000 | 10:1:11 | Trichloroethylene | 92 |

[1]The letters refers to the reactants as specifed in the text above.

ag) PEG 2300 methyl ether 16-hexadecanoyloxyhexadecanoate

PEG 2300 methyl ether (10.000 g, 4.35 mmol) was dissolved in tetrahydrofuran (90 ml) and pyridine (0.413 g, 5.22 mmol) was added. 16-hexadecanoyloxyhexadecanoyl chloride (2.301 g, 4.35 mmol) was dissolved in tetrahydrofuran (10 ml) and added dropwise. After stirring for 3 days at room temperature, the mixture was filtered and the solvent was evaporated under reduced pressure. The residue (12.08 g) was purified on a silica column, eluted with chloroform with increasing methanol concentration (from 1% to 3% methanol in chloroform) to give 5.20 g (43%) of the title compound. $^1$H NMR (300 MHz, CDCl$_3$): δ 0.80–0.87 (m, CH$_3$), 1.21 (s, (br), CH$_2$), 1.53–1.62 (m, CH$_2$), 2.20–2.35 (m, CH$_2$CO), 3.34 (s, CH$_3$O), 3.61 (s, OCH$_2$CH$_2$O), 4.02 (t, COOCH$_2$CH$_2$O), 4.19 (t, COOCH$_2$CH$_2$O). $^{13}$C NMR (75 MHz, CDCl$_3$): δ 13.95, 22.49, 24.71, 24.83, 25.74, 28.45, 28.95, 29.07, 29.16, 29.28, 29.34, 29.40, 29.46, 31.72, 34.05, 34.21, 58.85, 63.15, 64.19, 69.01, 70.37, 71.73, 173.64, 173.82.

ah) PEG 5000 methyl ether 16-hexadecanoyloxyhexadecanoate)

PEG 5000 methyl ether (7.500 g, 1.50 mmol) was dissolved in toluene (90 ml) and dried by refluxing in a Dean Stark apparatus. Pyridine (0.143 g, 1.80 mmol) was added followed by addition (dropwise) of 16-hexadecanoyloxyhexadecanoyl chloride (1.191 g, 2.25 mmol) dissolved in toluene (10 ml). The mixture was heated to reflux and after stirring under reflux for 3 days the mixture was cooled to room temperature and precipitated into hexane. After filtering, the precipitate was washed with hexane and dried (MgSO$_4$). After evaporation under reduced pressure, the residue was purified on a silica column, eluted with chloroform with increasing methanol concentration (from 1% to 3% methanol in chloroform) to give 5.93 g (72%) of the title compound. $^1$H NMR (300 MHz, CDCl$_3$): δ 0.82–0.86 (m, CH$_3$), 1.22 (s, (br), CH$_2$), 1.53–1.62 (m, CH$_2$), 2.20–2.35 (m, CH$_2$CO), 3.34 (s, CH$_3$O), 3.61 (s, OCH$_2$CH$_2$O), 4.01 (t, COOCH$_2$CH$_2$O), 4.18 (t, COOCH$_2$O). $^{13}$C NMR (75 MHz, CDCl$_3$): δ 13.66, 22.21, 24.43, 24.54, 25.46, 28.17, 28.67, 28.79, 28.87, 28.99, 29.06, 29.11, 29.17, 31.44, 33.73, 33.93, 58.57, 62.87, 63.90, 68.72, 69.62, 69.86, 70.09, 71.45, 76.85, 173.35, 173.53.

ai) PEG 10000 methyl ether 16-hexadecanoyloxyhexadecanoate

PEG 10000 methyl ether (7.500 g, 0.75 mmol) was dissolved in toluene (140 ml) and pyridine (0.107 g, 1.35 mmol) was added. The solution was heated to 60° C. and 16-hexadecanoyloxyhexadecanoyl chloride (0.595 g, 1.12 mmol) dissolved in toluene (10 ml) was added dropwise. The mixture was heated to reflux and after stirring under reflux for 3 days the mixture was cooled to room temperature and precipitated into hexane. After filtering, the precipitate was washed with hexane and dried. Flash chromatography on a silica column, eluted with 5% methanol in chloroform, gave 5.39 g (68%) of the title compound. $^1$H NMR (300 MHz, CDCl$_3$): δ 0.84 (t, CH$_3$), 1.21 (s, (br), CH$_2$), 1.55–1.60 (m, CH$_2$), 2.20–2.35 (m, CH$_2$CO), 3.34 (s, CH$_3$O), 3.61 (s, OCH$_2$CH$_2$O), 4.01 (t, COOCH$_2$CH$_2$O), 4.18 (t, COOCH$_2$CH$_2$O). $^{13}$C NMR (75 MHz, CDCl$_3$): δ 13.94, 22.48, 24.70, 24.82, 25.73, 28.94, 29.05, 29.14, 29.26, 29.33, 29.39, 29.45, 31.71, 34.00, 58.84, 63.14, 68.99, 69.36, 69.86, 69.97, 70.01, 70.36, 70.74, 70.82, 70.86, 71.72, 77.10, 173.62, 173.80.

aj) 16-[ω-Methoxy-PEG 2000-carbonyloxy]hexadecanoic acid 1-[16-(16-hexadecanoyloxyhexadecanoyloxy)-hexadecanoyloxy]ethyl ester Methoxy PEG 2000 chloroformate (1.90 g, 0.95 mmol) was dissolved in toluene (90 ml), and pyridine (0.09 g, 1.13 mmol) was added. 1[[16-(16-hexadecanoyloxyhexadecanoyloxy)hexadecanoyloxy]ethyl 16-hydroxyhexadecanoate (1.00 g, 0.95 mmol) was dissolved in toluene (10 ml) and added dropwise. The mixture was heated to reflux and after stirring under reflux for 10 hours, the mixture was cooled to room temperature and filtered. The solvent was evaporated under reduced pressure. The residue was purified on a silica column using chloroform containing 2% methanol, to give 1.00 g (35%) of the title compound. $^1$H-NMR (300 MHz, CDCl$_3$): δ 0.85 (t, CH$_3$), 1.20–1.33 (m, CH$_2$), 1.45 (d, —O—CH(CH$_3$)—O), 1.5–1.7 (m, CH$_2$), 2.0 (H$_2$O), 2.2–2.3 (m, —CH$_2$—C(O)—O), 3.35 (s, CH$_3$—O—), 3.5–3.7 (s, —OCH$_2$CH$_2$O—), 4.03 (t, —C(O)—O—CH$_2$—), 4.10 (t, —CH$_2$—O—C(O)—O—), 4.26 (m, —O—C(O)—O—CH$_2$—CH$_2$—O—), 6.8–6.9 (q, —O—CH(CH$_3$)—O). $^{13}$C-NMR (75 MHz, CDCl$_3$): δ 13.7, 19.2, 22.1, 24.2, 24.6, 25.2, 25.5, 28.2–29.2, 31.5, 33.9, 34.0, 58.7, 64.0, 66.3, 67.9, 68.5, 70.0, 71.5, 87.9, 171.5, 173.7.

ak) 16-[ω-Methoxy PEG 5000 carbonyloxy]hexadecanoic acid 1-[16-(16-hexadecanoyloxyhexadecanoyloxy)-hexadecanoyloxy]ethyl ester Methoxy PEG 5000 chloroformate (8.50 g, 1.70 mmol) was dissolved in toluene (90 ml) and pyridine (0.146 g, 1.85 mmol) was added. 1-[16-(16-Hexadecanoyloxyhexadecanoyloxy)-hexadecanoyloxy] ethyl 16-hydroxyhexadecanoate (1.79 g, 1.70 mml) was dissolved in toluene (10 ml) and added dropwise. The mixture was heated to reflux and after stirring under reflux for 3 days the mixture was cooled to room temperature and filtered. The solvent was evaporated under reduced pressure and the residue was purified on a silica column, eluted with chloroform with increasing methanol concentration (from 3% to 5% a methanol in chloroform) to give 3.90 g (38%) of the title compound. $^1$H-NMR (300 MHz, CDCl$_3$): δ 0.85 (t, CH$_3$), 1.20–1.33 (m, CH$_2$), 1.45 (d, —O—CH(CH$_3$)—O), 1.5–1.7 (m, CH$_2$), 1.8 (H$_2$O), 2.2–2.3 (m, —CH$_2$—C(O)—O), 3.35 (s, CH$_3$—O—), 3.5–3.7 (s, —OCH$_2$CH$_2$O—), 4.03 (t, —C(O)—O—CH$_2$—), 4.10 (t, —CH$_2$—O—C(O)—O—), 4.26 (m, —O—C(O)—O—CH$_2$—CH$_2$—O—), 6.8–6.9 (q, —O—CH(CH$_3$)—O).

al) 16-[ω-Methoxy PEG 10000 carbonyloxy]hexadecanoic acid 1-[16-(16-hexadecanoyloxyhexadecanoyloxy) hexadecanoyloxy]ethyl ester Methoxy PEG 10000 chloroformate (7.50 g, 0.75 mmol) was dissolved in toluene (90 ml), and pyridine (0.063 g, 0.80 mmol) was added. 1-[16-(16-Hexadecanoyloxyhexadecanoyloxy)-hexadecanoyloxy] ethyl 16-hydroxyhexadecanoate (0.79 g, 0.75 mmol) was dissolved in toluene (10 ml) and added dropwise. The mixture was heated to reflux and after stirring under reflux for 3 days the mixture was cooled to room temperature and filtered. The solvent was evaporated off under reduced pressure. The residue was purified on a silica column, eluted with chloroform with increasing methanol concentration (from 3% to 5% methanol in chloroform) to give 1.60 g (19%) of the title compound. $^1$H-NMR (300 MHz, CDCl$_3$): δ 0.85 (t, CH$_3$) 1.20–1.33 (m, CH$_2$), 1.45 (d, —O—CH(CH$_3$)—O), 1.5–1.7 (m, CH$_2$), 2.2–2.3 (m, —CH$_2$—C(O)—O), 3.35 (s, CH$_3$—O—), 3.5–3.7 (s, —OCH$_2$CH$_2$O—), 4.03 (t, —C(O)—O—CH$_2$), 4.10 (t, —CH$_2$—O—C(O)—O—), 4.26 (m, —O—C(O)—O—CH$_2$—CH$_2$—O—), 6.8–6.9 (q, —O—CH(CH$_3$)—O).

EXAMPLE 3

Preparation of Polymer Particles a–e) General procedure

A solution of copolymer in toluene was prepared. This solution was added to water (25–30% toluene v/v) and mixed with a high speed mixer (20500 rpm for 40 to 60 seconds). The resultant emulsion was freeze dried resulting in a fine white powder.

| Example | Polymer from Example 2 | Concentration of copolymer in Toluene (wt/wt) |
| --- | --- | --- |
| 3a | a | 10 |
| 3b | b | 10 |
| 3c | c | 10 |
| 3d | d | 10 |
| 3e | e | 10 | f) Particles from polymner of Example 2(f)

Polymer from Example 2(f) (70 mg) was dissolved in toluene (1 ml) and added to water (3 ml). The mixture was hand shaken for 30 seconds, frozen with dry ice/methanol and freeze dried.

g) Particles from polymer of Example 2(g)

Polymer from Example 2(g) (100 mg) was dissolved in toluene (1 ml) and added to water (3 ml). The mixture was hand shaken for 30 seconds, frozen with dry ice/methanol and freeze dried.

h–i) Particles from AB block copolymers of PEG, polycaprolactone and poly(lactic acid)

General procedure:

A solution of the block copolymer was prepared in toluene. Ca. 2 ml of solution was added to 10 ml of water with, in some cases, an extraneous emulsifier dissolved in the water. The mixture was mixed with a high speed mixer. The sample was immediately frozen and freeze dried to give a fine white powder.

| Example | Block copolymer from Example No./concentration | Extraneous emulsifier | Mixer speed (rpm) | Mixer time (seconds) |
|---|---|---|---|---|
| 3h | 2p/13 wt % | 2.5 wt % pluronic F68 | 8,000 | 15 |
| 3i | 2p/13 wt % | 1.25 wt % pluronic F68 | 8,000 | 15 |
| 3j | 2p/13 wt % | 0.63 wt % pluronic F68 | 8,000 | 15 |
| 3k | 2p/10 wt % | none | 8,000 | 15 |
| 3l | 2n/10 wt % | none | 8,000 | 15 | m–p) Particles from Poly(Methyl Methacylate)—graft-PEGs

General Procedure

A solution of the graft copolymer was prepared in toluene. Ca. 2 ml of solution was added to 10 ml of water with, in some cases, an extraneous emulsifier dissolved in the water. The mixture was mixed with a high speed mixer. The sample was immediately frozen and freeze dried to give a fine white powder.

| Example | Graft copolymer from Example No/concentration | Extraneous emulsifier | Mixer speed (rpm) | Mixer time (seconds) |
|---|---|---|---|---|
| 3m | 2t/4 wt % and 2y/6 wt % | none | 20500 | 30 |
| 3n | 2w/5 wt % and 2y/5 wt % | none | 8000 | 30 |
| 3o | 2w/6 wt % and 2y/4 wt % | none | 20500 | 30 |
| 3p | 2w/5 wt % and 2y/5 wt % | 1.0 wt % pluronic F68 | 8000 | 30 | q) Particles from block copolymer of methylene bis(16-hydroxyhexadecanoate), adipoyl chloride and α-hydroxy-ω-methoxy PEG 2000

The polymer of Example 2(i) (0.1 g) was dissolved in 1.9 g toluene and mixed for one minute with 3 ml water using aan Ystral mixer at 10,000 rpm to form a water-in-oil emulsion. The water-in-oil emulsion was then emulsified in water (3 ml) to form a water-in-oil-in-water emulsion, which was freeze dried to give air-filled particles.

r) Particles from block copolymer of methylene bis(16-hydroxyhexadecanoate), adinoyl chloride and α-hydroxy-ω-methoxy PEG 2000

The procedure of Example 3(q) was repeated except that the second water phase of the water-in-oil-in-water emulsion contained 2% gelatin.

s) Preparation of microbubbles of extended polymer from Example 2(ab) filled with perfluoro-n-butane (by shaking)

Polymer from Example 2(ab) (0.02 g) was dissolved in distilled water (1 ml). The solution was degassed, and the headspace of the vessel was filled with perfluoro-n-butane. The solution was shaken for 18 seconds on a Capmix®. Perfluoro-n-butane-filled microbubbles of a size suitable for intravenous administration were observed by microscopy. The microbubbles were stable for several days.

t) Preparation of micrabubbles of extended polymer from Example 2(ab) filled with perfluoro-n-butane (by sonicating)

Polymer from Example 2(ab) (0.25 g) was dissolved in distilled water (5 ml). The solution was degassed and then treated with a sonicator for 1 minute under a stream of perfluoro-n-butane. Perfluoro-n-butane-filled microbubbles of a size suitable for intravenous administration were observed in a microscope. The microbubbles were stable for several days.

u) Preparation of microbubbles of extended polymers from Examples 2(ab) and 2(ai) filled with perfluoro-n-butane (by shaking)

Polymer from Example 2(ab) (0.01 g) was dissolved in distilled water (0.5 ml) and added to 0.5 ml of an aqueous solution (1%) of the polymer from Example 2(ai). The solution was degassed, and the headspace of the vessel was filled with perfluoro-n-butane and shaken for 99 seconds on a Capmix®. Perfluoro-n-butane-filled microbubbles of a size suitable for intravenous administration were observed in a microscope. The microbubbles were stable for several days.

v) Preparation of microbubbles of Hypermer B246 filled with perfluoro-n-butane (by shaking)

Hypermer B246® (0.01 g) (ICI) was dissolved in 1 ml of a solution of 4.1% (weight) glycerol and 1.40 (weight) propylene glycol in water. The sample was degassed, and the headspace of the vessel filled with perfluoro-n-butane and shaken for 99 seconds on a Capmix®. Stable perfluoro-n-butane-filled microbubbles of a size suitable for intravenous administration were observed in a microcope.

EXAMPLE 4

Acoustic Characterisations (in-vitro)

General procedure

The samples were re-dispersed in MilliQ™ water by shaking on a laboratory shaker for an appropriate time. The dispersions were then observed by light microscopy to determine the particle size.

| Example | Particles from Example 3 | Particle size (μm) |
|---|---|---|
| 4a | a | 3–35 |
| 4b | b | 5–70 |
| 4c | c | 3–15 |
| 4e | e | 1–5 |
| 4f | f | 50–70 |
| 4g | g | 1–5 |
| 4h | h | 2–12 |
| 4i | i | 4–10 |
| 4j | j | 3–12 |
| 4k | k | 4–12 |
| 4l | l | 1–12 |
| 4m | m | 2–25 |
| 4n | n | 4–20 |
| 4o | o | 2–40 |
| 4p | p | 2–44 |

The particles were characterised by measuring the ultrasonic tramsmission through aqueous dispersions of the particles using a 3.5 MHz broad band transducer in a pulse-reflection technique. The aqueous solvent was used as a reference.

| Example | Particles from Example 3 | Result |
| --- | --- | --- |
| 4a | a | Contrast |
| 4b | b | Contrast |
| 4c | c | Contrast |
| 4d | d | Contrast |
| 4e | e | Contrast |
| 4g | g | Contrast |
| 4h | h | Contrast |
| 4i | i | Contrast |
| 4j | j | Contrast |
| 4k | k | Contrast |
| 4l | l | Contrast |
| 4m | m | Contrast |
| 4n | n | Contrast |
| 4o | o | Contrast |
| 4p | p | Contrast |

What is claimed is:

1. A microparticulate ultrasound contrast agent comprising microparticles which comprise gas microbubbles encapsulated by a non-polymerizable wall-forming block copolymer surfactant containing one or more hydrophilic regions or domains consisting essentially of polyethylene glycol units and one or more hydrophobic regions or domains selected from the group consisting of polylactic acids, polyglycolic acids and ethers and esters thereof, and polylactic acid/polyglycolic acid copolymers, wherein said gas microbubbles comprise gas selected from the group consisting of nitrogen, oxygen, hydrogen, nitrous oxide, carbon dioxide, helium, argon, sulphur hexafluoride and optionally fluorinated low molecular weight hydrocarbons which are in gaseous form at 37° C.

2. A contrast agent as claimed in claim 1 wherein the microparticles further comprise at least one additive selected from the group consisting of fatty acids and carbohydrate and triglyceride esters thereof, phospholipids, proteins and polyethylene glycols.

3. A contrast agent as claimed in claim 1 wherein said gas microbubbles comprise perfluorobutane or perfluoropentane.

* * * * *